(12) United States Patent
Ueno et al.

(10) Patent No.: US 7,510,282 B2
(45) Date of Patent: Mar. 31, 2009

(54) OPHTHALMIC PHOTOGRAPHING APPARATUS

(75) Inventors: Tokio Ueno, Nagoya (JP); Toshio Murata, Okazaki (JP)

(73) Assignee: Nidek Co., Ltd., Gamagori (JP)

( * ) Notice: Subject to any disclaimer, the term of this patent is extended or adjusted under 35 U.S.C. 154(b) by 53 days.

(21) Appl. No.: 11/878,721

(22) Filed: Jul. 26, 2007

(65) Prior Publication Data

US 2008/0024721 A1 Jan. 31, 2008

(30) Foreign Application Priority Data

Jul. 27, 2006 (JP) .............................. 2006-204425

(51) Int. Cl.
*A61B 3/10* (2006.01)
*A61B 3/14* (2006.01)

(52) U.S. Cl. ...................................... 351/206; 351/205

(58) Field of Classification Search ......... 351/205–221, 351/239, 246
See application file for complete search history.

(56) References Cited

U.S. PATENT DOCUMENTS 5,847,806 A 12/1998 Mihashi 6,726,325 B2 * 4/2004 Xie et al. .................... 351/209
6,769,769 B2 8/2004 Podoleanu et al.
7,290,881 B2 * 11/2007 Matsumoto ................. 351/214

FOREIGN PATENT DOCUMENTS

| JP | A 10-033484 | 2/1998 |
| JP | A 11-253403 | 9/1999 |
| JP | A 2005-230202 | 9/2002 |
| JP | A 2005-531346 | 10/2005 |
| WO | WO 2004/002298 A1 | 1/2004 |

* cited by examiner

*Primary Examiner*—Mohammed Hasan
(74) *Attorney, Agent, or Firm*—Oliff & Berridge, PLC

(57) ABSTRACT

An ophthalmic photographing apparatus which is easy to use and can simultaneously display OCT and SLO images as moving images while lightening a burden upon an examinee, the apparatus including an interference optical system having a first light source and a first scanning device which scans an examinee's eye with light from the first light source and obtaining a tomographic image of the eye, and a confocal optical system having a second light source and a second scanning device which scans the eye with light from the second light source and obtaining a front image of the eye, a changeover device which substantially makes a changeover of the light which is irradiated onto the eye alternately between the first light and the second light, a display device, and a display control unit displaying the images side by side as moving images on the display device.

6 Claims, 2 Drawing Sheets

OPHTHALMIC PHOTOGRAPHING APPARATUS

BACKGROUND OF THE INVENTION

1. Field of the Invention

The present invention relates to an ophthalmic photographing apparatus which obtains a tomographic image of an examinee's eye.

2. Description of Related Art

Conventionally, as an ophthalmic photographing apparatus which obtains a tomographic image of an examinee's eye in a non-invasive method, there is known an apparatus which includes an OCT (optical coherence tomography) optical system. In addition, such an apparatus is proposed that the OCT optical system is combined with an SLO (scanning laser opthalmoscope) optical system to obtain the tomographic image (hereinafter, referred to also as an OCT image) and a front image (hereinafter, referred to also as an SLO image) of the examinee's eye (see International Publication No. WO 2004/002298 corresponding to Japanese Patent application Unexamined Publication No. 2005-531346).

In this type of apparatus, it is convenient if the obtained SLO image is displayed as a moving image and the OCT image at a photographing position set on the displayed SLO image is obtained so as to be observable together with the SLO image. In the case of the apparatus disclosed in International Publication No. WO 2004/002298, however, since a scanning system (scanning device) which scans photographing light (measurement light) is shared by the OCT optical system and the SLO optical system, the OCT image and the SLO image cannot be simultaneously displayed as moving images. In addition, in obtaining the OCT image and the SLO image simultaneously, the amount of light which enters the examinee's eye should be adjusted so as not to be a burden upon the examinee.

SUMMARY OF THE INVENTION

An object of the invention is to overcome the problems described above and to provide an ophthalmic photographing apparatus which is easy to use, and can simultaneously display an OCT image and an SLO image as moving images while lightening a burden upon an examinee.

To achieve the objects and in accordance with the purpose of the present invention, an ophthalmic photographing apparatus includes an interference optical system having a first light source which emits low coherent light and a first scanning device which one-dimensionally or two-dimensionally scans an examinee's eye with the light emitted from the first light source which is defined as first photographing light and arranged to obtain a tomographic image of the eye by photo-receiving interference light which is obtained by synthesizing the first photographing light reflected from the eye and reference light which is generated from the light emitted from the first light source and has variable optical path length, a confocal optical system having a second light source and a second scanning device which two-dimensionally scans the eye with light emitted from the second light source which is defined as second photographing light and arranged to obtain a front image of the eye by photo-receiving the second photographing light reflected from the eye, a changeover device which substantially makes a changeover of the light which is irradiated onto the eye alternately between the first photographing light which is irradiated onto the eye via the interference optical system and the second photographing light which is irradiated onto the eye via the confocal optical system, a display device, and a display control unit arranged to display the tomographic image obtained via the interference optical system and the front image obtained via the confocal optical system side by side as moving images on the display device.

Additional objects and advantages of the invention are set forth in the description which follows, are obvious from the description, or may be learned by practicing the invention. The objects and advantages of the invention may be realized and attained by the ophthalmic photographing apparatus in the claims.

BRIEF DESCRIPTION OF THE DRAWINGS

The accompanying drawings, which are incorporated in and constitute a part of this specification, illustrate embodiments of the present invention and, together with the description, serve to explain the objects, advantages and principles of the invention. In the drawings.

DETAILED DESCRIPTION OF THE PREFERRED EMBODIMENTS

Figure 1:
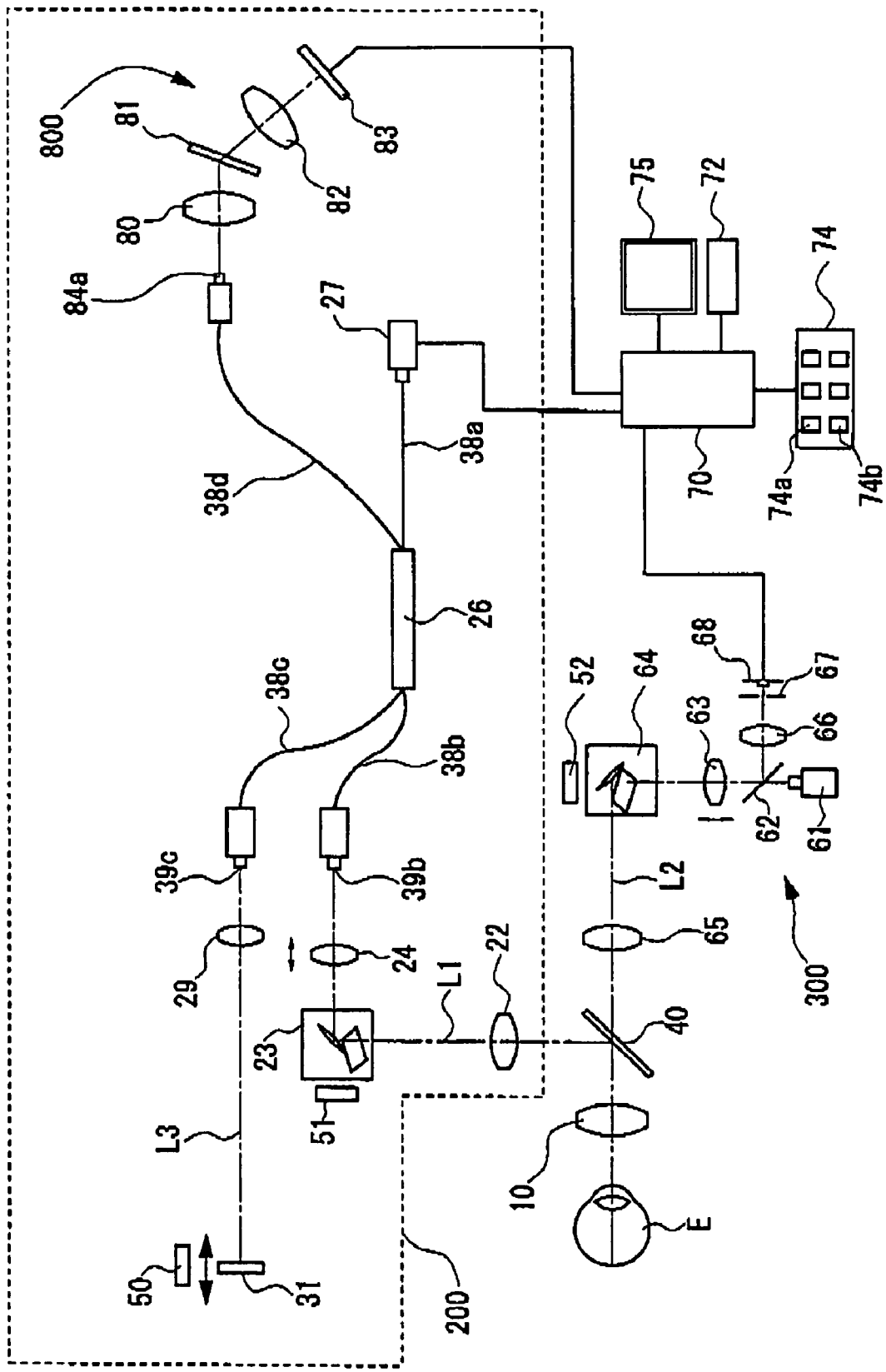
FIG. 1 is a view showing a schematic configuration of an optical system and a control system of an ophthalmic photographing apparatus according to a preferred embodiment of the present invention.

A detailed description of an ophthalmic photographing apparatus according to one preferred embodiment of the present invention will now be provided with reference to the accompanying drawings. FIG. 1 is a view showing a schematic configuration of an optical system and a control system of the ophthalmic photographing apparatus according to the preferred embodiment of the present invention. Hereinafter, a depth direction of an examinee's eye E (the direction of an optical axis L1 and an optical axis L2 which are described later) is referred to as a Z-direction, a horizontal direction orthogonal to the Z-direction is referred to as an X-direction, and a vertical direction orthogonal to the Z-direction is referred to as a Y-direction.

The optical system of the present apparatus includes an OCT (optical coherence tomography) optical system 200 that is an interference optical system, and an SLO (scanning laser opthalmoscope) optical system 300 that is a confocal optical system.

A dichroic mirror 40 has a property of reflecting first photographing light (e.g., infrared light with wavelengths in the vicinity of 840 nm) which is emitted from a light source 27 of the OCT optical system 200, and a property of transmitting second photographing light (e.g., infrared light with wavelengths in the vicinity of 780 nm) which is emitted from a light source 61 of the SLO optical system 300. Accordingly, the dichroic mirror 40 makes the optical axis L1 of the OCT optical system 200 coaxial with the optical axis L2 of the SLO optical system 300.

Firstly, a description of the OCT optical system 200 which is placed at a reflection side of the dichroic mirror 40 is provided. The light source 27 such as an SLD (Super Luminescent Diode) emits low coherent light. The light from the light source 27 passes through an optical fiber 38a that is a light guide, and is divided into the first photographing light and reference light by a fiber coupler 26 which functions as both a light dividing member and a light synthesizing member.

The first photographing light passes through an optical fiber 38b that is a light guide, exits from an end portion 39b of the fiber 38b, is transmitted through a relay lens 24 which is movable in a direction of the optical path L1 in accordance with refractive error of the eye E, is reflected by a scanning device 23 which includes a pair of (two) galvano-mirrors which are oscillated by a driving part 51, is transmitted through a relay lens 22, is reflected by the dichroic mirror 40, is transmitted through an objective lens 10, and is projected onto a fundus of the eye E and collected thereon.

Incidentally, the end portion 39b is placed at a position approximately conjugate with the fundus of the eye E, and the scanning device 23 (the galvano-mirrors) is placed at a position approximately conjugate with a pupil of the eye E. The scanning device 23 is not limited to the above-described type, and a known scanning device may be used.

The first photographing light reflected from the fundus travels on the optical path in the reverse direction to the direction at the time of the projection, and reaches the fiber coupler 26.

Meanwhile, the reference light passes through an optical fiber 38c that is a light guide, exits from an end portion 39c of the fiber 38c, is transmitted through a collimator lens 29 so as to be made into parallel light, is projected onto and reflected by a reference mirror 31 which is moved in a direction of an optical axis L3 by a driving part 50, and then travels on the optical path in the reverse direction to the direction at the time of the projection and reaches the fiber coupler 26.

The first photographing light reflected from the fundus and the reference light reflected by the reference mirror 31 are synthesized by the fiber coupler 26 so as to be made into interference light, and passes through an optical fiber 38d that is a light guide, exits from an end portion 84a of the fiber 38d, and enters a spectral optical system (spectrometer) 800 for dispersing the interference light into frequency components in order to obtain respective interference signals for the frequencies.

In the spectral optical system 800, the interference light is transmitted through a collimator lens 80 so as to be made into parallel light, is transmitted through a grating mirror (diffraction grating) 81 so as to be dispersed into the frequency components, is transmitted through a condenser lens 82, and is collected on a photo-receiving surface of a photodetector 83 having sensitivity to an infrared range. Accordingly, spectral information on interference fringes is recorded at the photodetector 83. Then, the spectral information is inputted into a calculation and control part 70 and analyzed by performing a Fourier transform thereon, whereby depth information on the eye E is obtained.

The calculation and control part 70 controls the driving part 50 to change optical path length of the reference light, and controls the driving part 51 to one-dimensionally scan the first photographing light on the fundus in the X-direction or the Y-direction, whereby a tomographic image (hereinafter, referred to also as an OCT image) of the fundus on an X-Z plane or a Y-Z plane is obtained. The obtained OCT image is stored in a memory 72 which is connected to the calculation and control part 70.

Incidentally, also a three-dimensional tomographic image (OCT image) of the fundus can be obtained by changing the optical path length of the reference light and two-dimensionally scanning the first photographing light on the fundus in the X-direction and the Y-direction.

Next, a description of the SLO optical system 300 which is placed at a transmission side of the dichroic mirror 40 is provided. The light source 61 such as an LD (Laser Diode) omits high coherent light. The second photographing light from the light source 61 is transmitted through a half mirror 62 and a relay lens 63 which is movable in a direction of the optical path L2 in accordance with the refractive error of the eye E, is reflected by a scanning device 64 which includes a galvano-mirror which is oscillated by a driving part 52 and a polygon mirror which is rotated by the driving part 52, is transmitted through a relay lens 65, the dichroic mirror 40 and the objective lens 10, and is projected onto the fundus of the eye E and collected thereon.

Incidentally, the scanning device 64 (the galvano-mirror and the polygon mirror) is placed at a position approximately conjugate with the pupil of the eye E. The scanning device 64 is not limited to the above-described type, and a known scanning device may be used.

The second photographing light reflected from the fundus travels on the optical path in the reverse direction to the direction at the time of the projection, is reflected by the half mirror 62, is transmitted through a condenser lens 66, passes through an opening 67, and is collected on a photo-receiving surface of a photodetector 68 having sensitivity to the infrared range. Then, detected signals from the photodetector 68 are inputted into the calculation and control part 70, and based on the detected signals, the calculation and control part 70 obtains a front image (hereinafter, referred to also as an SLO image) of the fundus. The obtained SLO image is stored in the memory 72.

Incidentally, the opening 67 is placed at a position approximately conjugate with the fundus.

A monitor (display device) 75 is connected to the calculation and control part 70 so as to be controlled. In addition, the calculation and control part 70 is connected with an operation part 74 which includes a photographing start switch 74a, a photographing position setting switch 74b, and the like.

Figure 2:
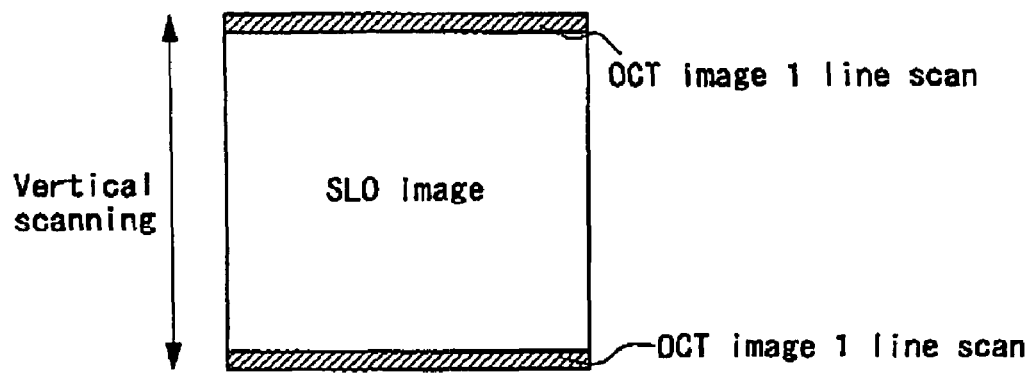
FIG. 2 is a view for illustrating the operation of the apparatus at the time of photographing an OCT image and an SLO image in succession.

Next, a description of a method for photographing the OCT image on the X-Z plane is provided. FIG. 2 is a view for illustrating the operation of the apparatus at the time of photographing the OCT image and the SLO image in succession. The calculation and control part 70 makes a changeover between irradiation with the first photographing light via the OCT optical system 200 and irradiation with the second photographing light via the SLO optical system 300 by turning on and off the light source 27 and the light source 61 alternately in order to prevent one photographing light from being irradiated onto the eye E during the time when the other photographing light being used for image obtainment is irradiated onto the eye E. Accordingly, photo-receiving signals from the photodetector 83 and photo-receiving signals from the photodetector 68 are inputted into the calculation and control part 70 in succession.

A time for obtaining the OCT image is mainly determined by a response time (an exposure time and a transfer time) of the photodetector 83. In this preferred embodiment, a photodetector having a response time of about $1/58000$th second is used for the photodetector 83. Accordingly, a time necessary for obtaining one line of OCT image is computed based on the number of recording pixels, and for example, the time is computed at about 0.0044 seconds for an image of 256 pixels, and about 0.0177 seconds for an image of 1024 pixels.

Meanwhile, a time for obtaining the SLO image is mainly determined by a scanning speed of the second photographing light in a lateral direction. In this preferred embodiment, the second photographing light is scanned in the lateral direction by the polygon mirror with 12 surfaces which can be rotated about 500 times per second, so that scanning of about 6000 times per second is possible. Accordingly, a time necessary for obtaining one line of SLO image is computed at about 0.00017 seconds, and, for example, in order to obtain an area (i.e., an area with field angles of 40°×40°) of one frame (1024×1024 pixels), a time computed as follows is needed: 0.00017 seconds×1024=about 0.1741 seconds (about 6 fps (frame per second)). Besides, when the second photographing light is made to reciprocate in a vertical direction, one frame of SLO image is obtained during the scan from top to bottom and another one frame of SLO image is obtained during the scan from bottom to top.

The calculation and control part 70 defines respective portions at the top end and the bottom end in a scanning area for one frame of SLO image (the hatched portions in FIG. 2.), the portions having little effect on the SLO image obtainment, as a region corresponding to the necessary time for the OCT image obtainment, and in this region, the light source 61 is turned off, and while the light source 61 is off, the light source 27 is turned on and the OCT image is obtained.

The calculation and control part 70 calculates the number of scanning lines in the vertical direction in the SLO image obtainment in accordance with the necessary time for the OCT image obtainment and then defines the scanning lines of that number so as to be equally defined from the top end and the bottom end of the area for the SLO image obtainment. During the time when the second photographing light is scanned by the scanning device 64, the calculation and control part 70 controls to turn off the light source 61 and turn on the light source 27 instead only when the second photographing light falls on portions including the defined scanning lines. When one frame of the SLO image is 1024×1024 pixels, the light source 61 is turned off for 0.0177 seconds, and the light source 27 is turned on instead for 0.0177 seconds. While the light source 27 is on, at least one frame of OCT image is obtained. The calculation and control part 70 controls to perform operations as such in succession, and simultaneously displays the alternately obtained OCT image and SLO image as moving images on the monitor 75.

As described above, since the light source 27 and the light source 61 are turned on and off alternately, even if the outputs of the light source 27 and the light source 61 are increased in order to improve photographic sensitivity of the OCT image and the SLO image, a burden onto the eye E is made small.

A description of the operation of the apparatus having a configuration as described above is provided. Alignment of the apparatus (the optical axes L1 and L2) with the eye E is performed, and a desired section of the fundus of the eye E is guided by making the examinee gaze at an unillustrated movable fixation lamp. In addition, the fundus is brought into focus based on the SLO image displayed on the monitor 75 (see FIG. 3).

Figure 3:
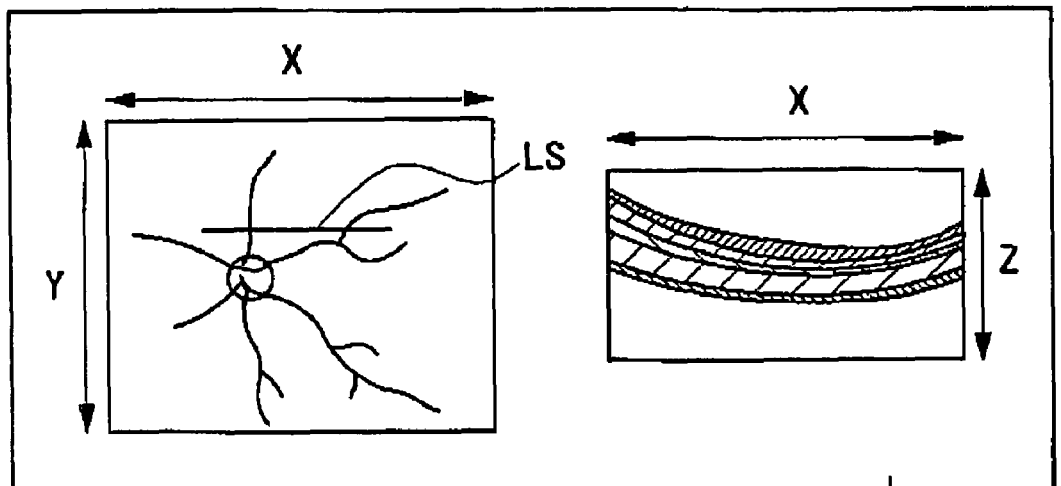
FIG. 3 is a view showing an OCT image and an SLO image of a fundus, which are displayed side by side on a monitor.

When the photo-receiving signals from the photodetector 83 are detected, the calculation and control part 70 controls to turn on and off the light source 27 and the light source 61 alternately so as to obtain the OCT image and the SLO image alternately, and simultaneously displays the obtained OCT image and SLO image side by side as moving images on the monitor 75. FIG. 3 is a view showing the OCT image and the SLO image of the fundus, which are displayed side by side on the monitor 75. At this time, the calculation and control part 70 controls to respectively renew the OCT image and the SLO image displayed on the monitor 75 every time one frame of OCT image and one frame of SLO image are obtained. By doing this, the OCT image and the SLO image can be observed nearly simultaneously at video rate. Besides, the initial (reference) photographing position for the OCT image is set as, for example, an approximately center position of the SLO image.

When the OCT image and the SLO image are displayed on the monitor 75, a photographing position for the OCT image is set on the SLO image on the monitor 75 which is observed in real time. A line LS for indicating the photographing position of the OCT image, which is electrically displayed on the SLO image by operation of the switch 74b, is moved on the SLO image 30 as to set the photographing position of the OCT image. When the line LS in the X-direction is set, the OCT image on the X-Z plane is obtained, and when the line LS in the Y-direction is set, the OCT image on the Y-Z plane is obtained. Besides, the line LS can be set to have a desired shape.

Based on the set photographing position, the OCT image on the X-Z plane is obtained. That is to say, since the relationship between the display position of the line LS on the monitor 75 and the scanning (irradiation) position of the first photographing light by the scanning device 23 is predetermined, based on the display position of the line LS which is set on the SLO image, the calculation and control part 70 drives and controls the scanning device 23 to scan the first photographing light so as to obtain the OCT image. Then, the calculation and control part 70 displays the obtained OCT image on the monitor 75. When the desired OCT image is displayed on the monitor 75 in this manner, the OCT image and the SLO image are photographed by operation of the switch 74a and stored in the memory 72.

Incidentally, correction of the OCT image can also be made by detecting a positional deviation of the eye E based on the SLO image at the time of the OCT image obtainment. In this case, by extracting a characteristic point of the fundus (e.g., a blood vessel or an optic papilla) from the obtained SLO image through image processing, and calculating a deviation amount of the extracted characteristic point, the positional deviation of the eye E can be detected. Then, the calculation and control part 70 drives and controls the scanning device 23 based on an amount of the detected positional deviation, and corrects the photographing position of the OCT image by an amount corresponding to the positional deviation (it is preferable to correct also the display position of the line LS). Accordingly, even if the eye E moves during photographing, the OCT image can be observed without being influenced by the eye movement.

Incidentally, in the above-described description, the SLO image and the OCT image which are displayed as moving images on the monitor 75 are, strictly speaking, images which are not simultaneously obtained but are obtained with a time difference. In a case where the time difference between the SLO image obtainment and the OCT image obtainment is small, assuming the SLO image and the OCT image, which are displayed as moving images on the monitor 75, to be simultaneously obtained and correspond to each other causes no substantial problem. In the preferred embodiment as shown in FIG. 3, since the time necessary for obtaining one frame of OCT image is 0.0177 seconds, a time difference of 0.0177 seconds arises between the SLO image and the OCT image displayed on the monitor 75. Meanwhile, a time necessary for obtaining one frame of SLO image is computed at about 0.1564 seconds (0.1741 seconds−0.0177 seconds), so that the time difference between the SLO image obtainment and the OCT image obtainment is extremely small. In addition, since the frequency of small movement of an eye at the time of eye fixation is said to be about 5 to 50 Hz, assuming the SLO image and the OCT image which is obtained at a designated position on the SLO image to be simultaneously obtained causes no substantial problem.

In the above description, the operation of the apparatus at the time of two-dimensional OCT image obtainment has been explained, however, the present invention is not limited thereto and can be applied also to a case of obtaining a three-dimensional OCT image.

Figure 4:
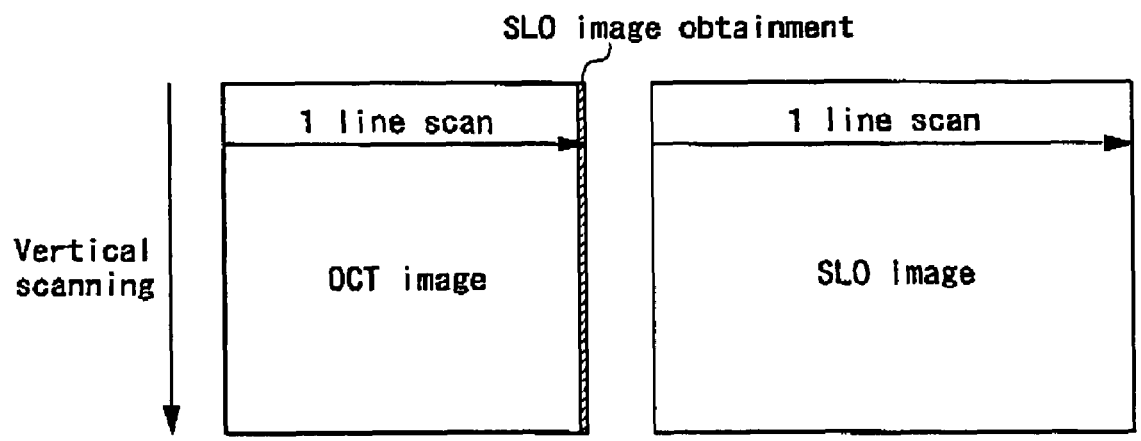
FIG. 4 is a view for illustrating the operation of the apparatus at the time of photographing a three-dimensional OCT image.

FIG. 4 is a view for illustrating the operation of the apparatus at the time of photographing the three-dimensional OCT image. In this case, the OCT image is obtained in 256×256 pixels. A time necessary for obtaining one line of SLO image is computed at about 0.00017 seconds, which corresponds to five pixels of the OCT image.

In obtaining one line of three-dimensional OCT image, the calculation and control part 70 controls to irradiate the first photographing light in most of a scanning area of the first photographing light for one line which is scanned by the scanning device 23, and to irradiate the second photographing light in the portion at the left end or the right end (the hatched portion in FIG. 4), which has little effect on the OCT image obtainment.

In other words, in obtaining 256 pixels of the first line of OCT image, the calculation and control part 70 controls to turn on the light source 27 until 251 pixels are obtained, and once 251 pixels are obtained, the light source 27 is turned off and the light source 61 is turned on. Then, scanning for the first line of SLO image is made, and the light source 61 is turned off and the light source 27 is turned on after 0.00017 seconds. By repeating this for 256 times, one frame (251×256 pixels) of three-dimensional OCT image and one frame of SLO image are obtained after about 2.3 seconds.

Incidentally, in the preferred embodiment, since the LD which emits the light with wavelengths in the vicinity of 780 nm is used for the light source 61 of the SLO optical system 300, it is possible to perform ICG (indocyanine green) fluorescent photographing by using this light as infrared excitation light for fluorescence.

In the preferred embodiment, the Fourier-domain OCT optical system is used for the reference optical system for obtaining the tomographic image of the examinee's eye. However, the present invention is not limited thereto and a time-domain OCT optical system may be used.

In the preferred embodiment, a fundus portion of the examinee's eye is made to be the subject photographed. However, the present invention is not limited thereto and a predetermined portion of the examinee's eye such as an anterior-segment portion of the examinee's eye may be the subject photographed.

In the preferred embodiment, the changeover between the irradiation with the first photographing light and the irradiation with the second photographing light is made by turning on and off the light source 27 and the light source 61 alternately. However, the present invention is not limited thereto and the changeover between the irradiation with the first photographing light and the irradiation with the second photographing light may be made by alternately passing or intercepting the light using a shutter or the like.

In addition, when the changeover of the light which is irradiated onto the examinee's eye is made between the first photographing light and the second photographing light, it is essential only that the changeover is substantial, and it is not necessary to prevent one photographing light from being irradiated during the time when the other photographing light is irradiated. For example, in order to prevent the total output of the first photographing light and the second photographing light which are simultaneously irradiated onto the examinee's eye from exceeding a predetermined upper limit, the output of one photographing light may be made lower than the output of the other photographing light being used for image obtainment.

In addition, it may be arranged that the eye is simultaneously irradiated with the first photographing light and the second photographing light, and the respective scanning devices are driven and controlled so that the irradiating (convergent) positions of the first photographing light and the second photographing light on the fundus differ from each other.

In the preferred embodiment, the OCT optical system 200 and the SLO optical system 300 are configured separately. However, the OCT optical system 200 and the SLO optical system 300 may be configured to share a portion thereof. For example, they may share the light source.

In the preferred embodiment, it is arranged that the OCT image is obtained while the respective portions at the top end and the bottom end in the scanning area for one frame of SLO image are scanned. However, the present invention is not limited thereto and it is essential only that the OCT image and the SLO image are obtained in succession.

Accordingly, the frame rate for one frame of SLO image may be reduced to one-second of its original frame rate (e.g., the number of frames of SLO image obtained in one second is reduced from 6 frames to 3 frames) so as to obtain the OCT image during the spare time.

The foregoing description of the preferred embodiment of the invention has been presented for purposes of illustration and description. It is not intended to be exhaustive or to limit the invention to the precise form disclosed, and modifications and variations are possible in the light of the above teachings or may be acquired from practice of the invention. The embodiments chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. An ophthalmic photographing apparatus comprising;
    an interference optical system including:
        a first light source which emits low coherent light; and
        a first scanning device which one-dimensionally or two-dimensionally scans an examinee's eye with the light emitted from the first light source, which is defined as first photographing light, and
    arranged to obtain a tomographic image of the eye by photo-receiving interference light which is obtained by synthesizing the first photographing light reflected from the eye, and reference light which is generated from the light emitted from the first light source and has variable optical path length;
    a confocal optical system including:
        a second light source; and
        a second scanning device which two-dimensionally scans the eye with light emitted from the second light source, which is defined as second photographing light, and
    arranged to obtain a front image of the eye by photo-receiving the second photographing light reflected from the eye;
        a changeover device which substantially makes a changeover of the light which is irradiated onto the eye alternately between the first photographing light which is irradiated onto the eye via the interference optical system and the second photographing light which is irradiated onto the eye via the confocal optical system;
        a display device; and a display control unit arranged to display the tomographic image obtained via the interference optical system and the front image obtained via the confocal optical system side by side as moving images on the display device.

2. The ophthalmic photographing apparatus according to claim 1, wherein the changeover device makes the changeover between the irradiation with the first photographing light and the irradiation with the second photographing light to obtain one frame of tomographic image and one frame of front image alternately.

3. The ophthalmic photographing apparatus according to claim 2, wherein the changeover device makes the changeover between the irradiation with the first photographing light and the irradiation with the second photographing light in order to prevent one photographing light from being irradiated onto the eye during the time when the other photographing light being used for image obtainment is irradiated onto the eye.

4. The ophthalmic photographing apparatus according to claim 3, wherein the changeover device makes the changeover between the irradiation with the first photographing light and the irradiation with the second photographing light by controlling to turn on and off the first light source and the second light source respectively.

5. The ophthalmic photographing apparatus according to claim 2, wherein the changeover device substantially makes the changeover between the irradiation with the first photographing light and the irradiation with the second photographing light by making, in order to prevent the total output of the first photographing light and the second photographing light which are simultaneously irradiated onto the eye from exceeding a predetermined upper limit, the output of one photographing light lower than the output of the other photographing light being used for image obtainment.

6. The ophthalmic photographing apparatus according to claim 5, wherein the changeover device substantially makes the changeover between the irradiation with the first photographing light and the irradiation with the second photographing light by controlling the respective output of the first light source and the second light source.

* * * * *